United States Patent [19]

Demerson et al.

[11] 4,323,572

[45] Apr. 6, 1982

[54] ANTIHYPERTENSIVE TRICYCLIC ISOINDOLE DERIVATIVES

[75] Inventors: Christopher A. Demerson, Montreal; Leslie G. Humber, Dollard des Ormeaux; Jean-Marie Ferland, St. Laurent, all of Canada

[73] Assignee: American Home Products Corporation, New York, N.Y.

[21] Appl. No.: 232,267

[22] Filed: Feb. 6, 1981

Related U.S. Application Data

[62] Division of Ser. No. 78,547, Sep. 24, 1979, Pat. No. 4,273,773.

[51] Int. Cl.³ .................. A61K 31/505; C07D 487/04
[52] U.S. Cl. .................. 424/251; 544/247; 544/252
[58] Field of Search ............... 544/252, 245, 246, 247, 544/250; 424/251

[56] References Cited

U.S. PATENT DOCUMENTS

| | | | |
|---|---|---|---|
| 2,993,047 | 7/1961 | Bortnick et al. | 544/252 X |
| 3,428,650 | 2/1969 | Houlihan | 544/246 X |
| 3,590,043 | 6/1971 | Graf | 424/251 X |
| 3,657,240 | 4/1972 | Sulkowski | 424/251 X |

*Primary Examiner*—Donald G. Daus
*Assistant Examiner*—D. G. Rivers
*Attorney, Agent, or Firm*—Arthur E. Wilfond

[57] ABSTRACT

Tricyclic isoindole derivatives characterized by having a 1,2,3,4,6,10b-hexahydropyrazino[2,1-a]isoindole or 1,3,4,10b-tetrahydropyrimido[6,1-a]isoindol-6(2H)-one nucleus are disclosed. The foregoing compounds are useful antihypertensive agents.

12 Claims, No Drawings

ANTIHYPERTENSIVE TRICYCLIC ISOINDOLE DERIVATIVES

This is a division of application Ser. No. 78,547, filed Sept. 24, 1979, now U.S. Pat. No. 4,273,773.

RELATED CASE

Certain compounds used as intermediates herein are disclosed in 1,3-DIHYDRO-3-(2-HYDROXYETHYL)-2H-ISOINDOL-1-ONE DERIVATIVES Ser. No. 78,546 of Wilbur Lippmann, Christopher A. Demerson, Jean-Marie Ferland and Leslie G. Humber, filed on even date herewith, now U.S. Pat. No. 4,244,966 application Ser. No. 78,548 of Wilbur Lippmann, METHOD OF USE AND COMPOSITION FOR 1,3-DIHYDRO-3-(2-HYDROXY-2-METHYLPROPYL)-2H-ISOINDOL-1-ONE, filed on even date herewith, now U.S. Pat. No. 4,267,189 also is related thereto.

BACKGROUND OF THE INVENTION (a) Field of the Invention

This invention relates to novel tricyclic isoindole derivatives, to useful intermediates, to processes for their preparation and to therapeutically acceptable acid addition salts and pharmaceutical compositions of the derivatives.

More specifically, the present invention relates to novel 1,2,3,4,6,10b-hexahydropyrazino[2,1-a]isoindole and 1,3,4,10b-tetrahydropyrimido[6,1-a]isoindol-6(2H)-one derivatives possessing valuable pharmacologic properties. These derivatives are useful for treating hypertension in mammals.

(b) Description of the Prior Art

Compounds having the tricyclic isoindole nucleus are known. For example, compounds having the pyrazino[2,1-a]isoindole nucleus are disclosed by M. Winn in U.S. Pat. No. 3,597,422, issued Aug. 3, 1971. This patent discloses 1,1-dimethyl-6-phenyl-1,2,3,4-tetrahydropyrazino[2,1-a]isoindole derivatives useful as fungicides.

Compounds having the pyrimido[6,1-a]isoindole nucleus have not been reported previously. However, isomeric pyrimidoisoindoles, for example, pyrimido[2,1-a]isoindoles, have been disclosed; for example, M. Winn and H. E. Zaugg, J. Org. Chem., 34, 249 (1969). The latter reference and M. Winn and H. E. Zaugg. J. Org. Chem., 33, 3779 (1968) are cited in U.S. Pat. No. 3,597,422, noted above.

SUMMARY OF THE INVENTION

The compounds of this invention are represented by formula I

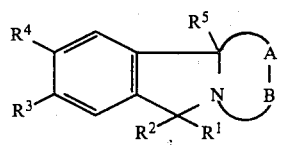

in which $R^1$ is hydrogen; $R^2$ is hydrogen, hydroxy or hydroxymethyl, or $R^1$ and $R^2$ together form a ketone; $R^3$ and $R^4$ each is hydrogen, lower alkoxy, lower alkyl, trifluoromethyl, halo or hydroxy, or $R^3$ and $R^4$ together form a OCH$_2$O chain; $R^5$ is hydrogen, lower alkyl or phenylmethyl; and A-B is a chain of formula CHR$^6$NR$^7$CR$^8$R$^9$CR$^{10}$R$^{11}$ wherein $R^6$ is hydrogen or lower alkyl; $R^7$ is hydrogen, lower alkyl, lower alkanoyl, cyclohexylcarbonyl, phenylmethyl, benzoyl, carboxymethyl, aminocarbonyl, 4-nitrobenzoyl, 4-aminobenzoyl, a radical of formula $(CH_2)_nNR^{12}R^{13}$ wherein n is an integer from two to six, and $R^{12}$ and $R^{13}$ each is hydrogen or lower alkyl, or a radical of formula $CO(CH_2)_{n-1}NR^{12}R^{13}$ wherein n, $R^{12}$ and $R^{13}$ are as defined herein; $R^8$, $R^9$, $R^{10}$ and $R^{11}$ each is hydrogen or lower alkyl; or $R^9$ and $R^{10}$ together form a $(CH_2)_4$ chain, and the carbon atom bearing $R^{10}$ and $R^{11}$ is attached to the nitrogen atom of formula I; or A-B is a chain of formula CH$_2$CR$^{14}$R$^{15}$NR$^{16}$CHR$^{17}$ wherein $R^{14}$ and $R^{15}$ each is hydrogen or lower alkyl; $R^{16}$ is hydrogen, a radical of formula $(CH_2)_n$NR$^{12}$R$^{13}$ wherein n, $R^{12}$ and $R^{13}$ are as defined herein or a radical of formula $CO(CH_2)_{n-1}$NR$^{12}$R$^{13}$ wherein n, $R^{12}$ and $R^{13}$ are as defined herein, and $R^{17}$ is hydrogen, or $R^{16}$ and $R^{17}$ together form an imine; and the carbon atom bearing $R^{17}$ is attached to the nitrogen atom of formula I; with the proviso that when $R^1$ is hydrogen, $R^2$ is hydrogen, hydroxy or hydroxymethyl, or $R^5$ is lower alkyl or phenylmethyl, then A-B is a chain of formula CHR$^6$NR$^7$CR$^8$-R$^9$CR$^{10}$R$^{11}$ wherein $R^6$, $R^7$, $R^8$, $R^9$, $R^{10}$ and $R^{11}$ are as defined herein and with the additional proviso that when A-B is a chain of formula CHR$^6$NR$^7$CR$^8$R$^9$CR$^{10}$R$^{11}$ wherein $R^6$ is lower alkyl then $R^1$, $R^2$, $R^5$, $R^8$ and $R^9$ are hydrogen, or $R^1$ and $R^2$ together form a ketone.

A preferred group of compounds of formula I are represented by formula Ib

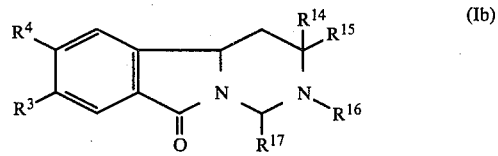

in which $R^3$ and $R^4$ each is hydrogen, lower alkoxy, lower alkyl, trifluoromethyl, halo, or hydroxy; or $R^3$ and $R^4$ together form a OCH$_2$O chain; $R^{14}$ and $R^{15}$ each is hydrogen or lower alkyl; $R^{16}$ is hydrogen, a radical of formula $(CH_2)_nNR^{12}R^{13}$ wherein n is an integer from two to six, and $R^{12}$ and $R^{13}$ each is hydrogen or lower alkyl, or a radical of formula $CO(CH_2)_{n-1}NR^{12}R^{13}$ wherein n, $R^{12}$ and $R^{13}$ are as defined herein, and $R^{17}$ is hydrogen, or $R^{16}$ and $R^{17}$ together form an imine.

A more preferred group of compounds of formula Ib are those in which $R^3$ and $R^4$ are hydrogen; $R^{14}$ and $R^{15}$ each is hydrogen or lower alkyl; $R^{16}$ is hydrogen or a radical of formula $CO(CH_2)_{n-1}NR^{12}R^{13}$ wherein n is an integer from two to six, and $R^{12}$ and $R^{13}$ each is lower alkyl; and $R^{17}$ is hydrogen, or $R^{16}$ and $R^{17}$ together form an imine.

The therapeutically acceptable acid addition salts of the compounds of formula I are also included within the scope of this invention.

This invention involves a pharmaceutical composition comprising a compound of formula I, or a therapeutically acceptable addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "lower alkanoyl" as used herein means straight chain alkanoyl radicals containing from two to six carbon atoms and a branched chain alkanoyl radical containing four carbon atoms and includes acetyl, propionyl, isobutyryl, hexanoyl and the like.

The term "lower alkanol" as used herein means both straight and branched chain alkanols containing from one to four carbon atoms and includes methanol, ethanol, isopropanol, butanol and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethylmorpholine, 1,5-diazabicyclo[3.4.0]nonene-5 and the like.

The term "complex metal hydride" as used herein means the metal hydrides, including lithium aluminum hydride, lithium aluminum hydride-aluminum chloride, aluminum hydride-aluminum chloride, borane, borane-methyl sulfide, sodium borohydride-aluminum chloride, diisobutylaluminum hydride and the like.

The basic compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic acetic, maleic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I. Such stereochemical isomers are obtained in substantially pure form by classical separation techniques and by sterically controlled synthesis and have arbitrarily been named as isomers A and B, respectively.

Individual optical enantiomers, which can be separated by fractional crystallization of the diastereomeric salts thereof, for instance, salts with d- or l-tartaric acid or D-(+)-α-bromocamphor sulfonic acid, are also included.

The antihypertensive effect of the compounds of formula I or therapeutically acceptable acid addition salts thereof is demonstrated in standard pharmacological tests, for example, in tests conducted in the spontaneously hypertensive rat (SHR) such as described by I. Varva, et al., Can. J. Physiol. Pharmacol., 51, 727 (1973). More specifically exemplified, the compounds of formula I are shown to be effective antihypertensive agents by using the testing method described in the latter publication. The latter test method is modified so that the test compound is administered to the rat by gastric gavage and the systolic blood pressure is measured by the tail-cuff method before administration of the compound and 1.0 to 4 hours thereafter. Using this method, the following representative compounds of formula I are effective for reducing the systolic blood pressure (BP) in the spontaneously hypertensive rat (the amount of test compound and its reduction in BP are indicated in the parentheses): 1,10b-dihydro-2,2-dimethylpyrimido[6,1-a]isoindol-6(2H)-one (at a dose of 25 mg/kg of body weight causes a 8 to 14% reduction in BP at 1 to 4 hours, described in Example 2), 1,3,4,10b-tetrahydro-2,2-dimethylpyrimido[6,1-a]isoindol-6(2H)-one (at a dose of 50 mg/kg of body weight causes a 8 to 11% reduction in BP at 1 to 4 hours, described in Example 3) and 1,3,4,10b-tetrahydropyrimido[6,1-a]isoindol-6(2H)-one (at a dose of 25 mg/kg of body weight causes a 8 to 14% reduction in BP at 1 to 4 hours, described in Example 5).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavouring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavouring agent and antioxidant.

The dosage of the compounds of formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. The effective antihypertensive amount of the compounds usually ranges from about 0.1 mg to about 250 mg per kilogram body weight per day, although as aforementioned variations will occur. However a dosage level that is in the range of from about 1.0 mg to about 100 mg per kilogram body weight per day is employed most desirably in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamterene and furosemide. Examples of still other suitable antihypertensive agents are prazosin, hydralazine and centrally active antihypertensive agents such as methyldopa, clonidine, and reserpine; as well as the β-adrenergic blocking agents, for instance, propranolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing diuretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physicians' Desk Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I, or its therapeutically acceptable salt is administered as described previously.

PROCESS

The process for the preparation of the compounds of formula I is illustrated by the following description of the different embodiments of this invention.

PREPARATION OF THE COMPOUNDS OF FORMULA Ib

Reaction scheme 1 illustrates a process for the preparation of the compounds of formula Ib in which $R^3$ and $R^4$ each is hydrogen, lower alkoxy, lower alkyl, halo or hydroxy; or $R^3$ and $R^4$ together form a $OCH_2O$ chain; $R^{14}$, $R^{16}$ and $R^{17}$ are hydrogen; and $R^{15}$ is hydrogen or lower alkyl.

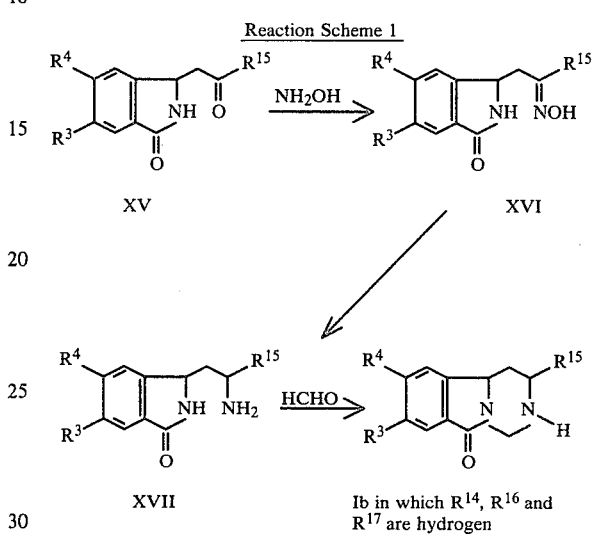

The starting materials of formula XV in which $R^3$, $R^4$ and $R^{15}$ are as defined herein are obtained by the appropriate conversion of a 2,3-dihydro-3-oxo-1H-isoindole-1-acetic acid derivative, which also is known as a 1,3-dihydro-3-oxo-2H-isoindole-1-acetic acid derivative. The latter compounds are either known, for example 2,3-dihydro-3-oxo-1H-isoindole-1-acetic acid is described by F. M. Rowe et al., J. Chem. Soc., 1098 (1936), or can be prepared by an analogous process to that described in the latter reference. One conversion of the 2,3-dihydro-3-oxo-1H-isoindole-1-acetic acid derivatives is the reaction of the latter compound with four to six molar equivalents of a lower alkyl lithium in an inert organic solvent, preferably tetrahydrofuran and/or diethyl ether, at 20° at 30° C. for two to five hours to obtain the corresponding compound of formula XV in which $R^3$ and $R^4$ are as defined herein and $R^{15}$ is lower alkyl. Another conversion of the 2,3-dihydro-3-oxo-1H-isoindole-1-acetic derivative is the reduction of the latter compound to obtain the corresponding aldehyde of formula XV in which $R^3$ and $R^4$ are as defined herein and $R^{15}$ is hydrogen.

It is necessary to convert the compound of formula XV to the corresponding amine of formula XVII. A preferred method of achieving this conversion is to react the compound of formula XV with about two molar equivalents of hydroxylamine hydrochloride and about three molar equivalents of potassium hydroxide in a mixture of water and ethanol at 80° to 100° C. for five to 30 minutes to obtain the corresponding oxime of formula XVI in which $R^3$, $R^4$ and $R^{15}$ are as defined herein. The latter compound is reduced, preferably with nickel-aluminum alloy and sodium hydroxide in a mixture of water and ethanol at 20° to 30° C. for one to four hours, to obtain the corresponding amine of formula XVII in which $R^3$, $R^4$ and $R^{15}$ are as defined herein.

In addition to the above described process for preparing an amine of formula XVII, other processes are available for preparing an amine of formula XVII. For instance, a preferred process for preparing an amine of formula XVII in which $R^3$ and $R^4$ are as defined herein and $R^{15}$ is hydrogen is the hydrogenation of a corresponding derivative of 3-cyanomethylenephthalimidine with hydrogen under a pressure of 700 psi at 70° C. in the presence of Raney-nickel catalyst in a solvent of ethanol saturated with ammonia. The 3-cyanomethylenephthaimidine derivatives are either known, for example, 3-cyanomethylenephthalimidine is described by J. Kranz, Chem. Ber., 100, 2261 (1967), or can be prepared by an analogous process to that described in the latter reference.

Once again, returning to a reaction scheme 1, the amine of formula XVII is condensed with three to five molar equivalents of formaldehyde, preferably in the form of 37% aqueous formaldehyde, in an inert organic solvent, preferably ethanol, at 80° to 100° C. for two to five hours to obtain the corresponding compound of formula Ib in which $R^3$, $R^4$ and $R^{15}$ are as defined herein, and $R^{14}$, $R^{16}$ and $R^{17}$ are hydrogen.

In addition to the process illustrated in reaction scheme 1, another process for the preparation of the compounds of formula Ib in which $R^3$, $R^4$, $R^{14}$ and $R^{15}$ are as defined herein, and $R^{16}$ and $R^{17}$ are hydrogen or $R^{16}$ and $R^{17}$ together form an imine is illustrated in reaction scheme 2. In other words, with regard to the imine, when $R^{16}$ and $R^{17}$ are joined together forming a bond, a cyclic imine is provided.

Reaction Scheme 2

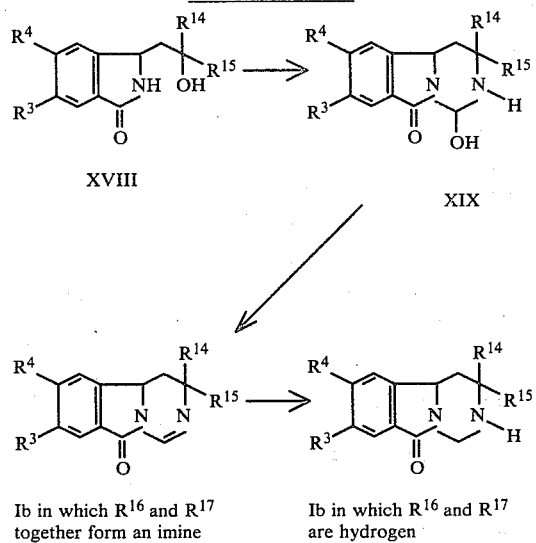

XVIII

XIX

Ib in which $R^{16}$ and $R^{17}
together form an imine

Ib in which $R^{16}$ and $R^{17}$
are hydrogen

Ib in which $R^{16}$ and $R^{17}$ together form an imine
Ib in which $R^{16}$ and $R^{17}$ are hydrogen With reference to reaction scheme 2, the starting materials of formula XVIII are obtained from the appropriate 2,3-dihydro-3-oxo-1H-isoindole-1-acetic acid derivative. For instance, reduction of the latter compound with a complex metal hydride, preferably lithium aluminum hydride or borane, in an inert organic solvent, preferably tetrahydrofuran or diethyl ether, at 0° to 30° C. for one to five hours gives the corresponding compound of formula XVIII in which $R^3$ and $R^4$ are as defined herein, and $R^{14}$ and $R^{15}$ are hydrogen. In another preparation of a compound of formula XVIII, the 2,3-dihydro-3-oxo-1H-isoindole-1-acetic acid derivative is esterified with a lower alkanol in the presence of an acid catalyst, preferably p-toluenesulfonic, at 60° to 80° C. for three to five hours to obtain the corresponding 2,3-dihydro-3-oxo-1H-isoindole-1-acetic acid lower alkyl ester derivative. Reaction of the latter compound with about two to ten molar equivalents of a lower alkyl magnesium halide, e.g. a lower alkyl magnesium chloride, bromide or iodide, in an inert organic solvent, preferably tetrahydrofuran and/or diethyl ether, at 30° to 50° C. for 3 to 30 hours gives the corresponding compound of formula XVIII in which $R^3$ and $R^4$ are as defined herein, and $R^{14}$ and $R^{15}$ each is the same lower alkyl.

The compounds of formula XV, described above and illustrated in reaction scheme 1, are also useful for preparing the alcohols of formula XVIII. For example, the compound of formula XV in which $R^3$ and $R^4$ are as defined herein and $R^{15}$ is lower alkyl are reduced with a complex metal hydride, preferably lithium aluminum hydride or sodium borohydride, to obtain the corresponding compound of formula XVIII in which $R^3$ and $R^4$ are as defined herein, $R^{14}$ is hydrogen and $R^{15}$ is lower alkyl. Another useful conversion of the compound of formula XV in which $R^3$ and $R^4$ are as defined herein and $R^{15}$ is lower alkyl is the reaction of the latter compound with about one to five molar equivalents of the Grignard reagent, $R^{14}$-magnesium halide, i.e. $R^{14}$-magnesium chloride, bromide or iodide, wherein $R^{14}$ is lower alkyl, in the same manner as described above, to obtain the corresponding compound of formula XVIII in which $R^3$ and $R^4$ are as defined herein, and $R^{14}$ and $R^{15}$ each is lower alkyl.

With reference to reaction scheme 2, the alcohol of formula XVIII is reacted with 1.5 to 2.0 molar equivalents of sodium cyanide in the presence of about 20 to 40 molar equivalents of sulfuric acid in a solvent of acetic acid at 20° to 30° C. for two to six hours to obtain the corresponding compound of formula XIX in which $R^3$, $R^4$, $R^{14}$ and $R^{15}$ are as defined herein.

Dehydration of the compound of formula XIX, preferably with 5 to 15 molar equivalents of thionyl chloride at 70° to 80° C. for one to five hours gives the corresponding hydrochloride salt of the compound of formula Ib in which $R^3$, $R^4$, $R^{14}$ and $R^{15}$ are as defined herein, and $R^{16}$ and $R^{17}$ together form an amine. If desired, the latter salt can be dissolved in a dilute solution of an aqueous alkali, preferably sodium hydroxide or sodium bicarbonate, and the solution is extracted with a water immiscible organic solvent, preferably ethyl acetate or chloroform, to obtain the corresponding compound of formula Ib in which $R^3$, $R^4$, $R^{14}$ and $R^{15}$ are as defined herein, and $R^{16}$ and $R^{17}$ together form an amine.

Reduction of the latter compound of formula Ib with a complex metal hydride, preferably with three to five molar equivalents of sodium borohydride in an inert organic solvent, preferably methanol, at 50° to 70° C. for one to three hours, gives the corresponding compound of formula Ib in which $R^3$, $R^4$, $R^{14}$ and $R^{15}$ are as defined herein, and $R^{16}$ and $R^{17}$ are hydrogen.

The compounds of formula Ib, prepared as described above, can be transformed to ther compounds of formula Ib. For this transformation, the compound of formula Ib in which $R^{16}$ and $R^{17}$ are hydrogen is reacted with about 1.1 to 1.5 molar equivalents of a compound of formula $X-CO-(CH_2)_{n-1}-X^1$ wherein n is an integer from two to six, and X and $X^1$ each is chloro, bromo or iodo in the presence of an organic proton acceptor, preferably triethylamine, in an inert organic solvent, preferably benzene, at 20° to 30° C. for 10 to 30 hours to give the corresponding intermediate having the radical CO—$(CH_2)_{n-1}$—$X^1$ in which n and $X^1$ are as defined herein. Subsequently, the latter intermediate is reacted with about 5 to 15 molar equivalents of an amine of formula $HNR^{12}R^{13}$ in which $R^{12}$ and $R^{13}$ each is hydrogen or lower alkyl in an inert organic solvent, preferably tetrahydrofuran, at 20° to 60° C. for one to ten hours to obtain the corresponding compound of formula Ib in which $R^3$, $R^4$, $R^{14}$ and $R^{15}$ are as defined herein, $R^{16}$ is a radical of formula $CO(CH_2)_{n-1}NR^{12}R^{13}$ wherein n, $R^{12}$ and $R^{13}$ are as defined herein, and $R^{17}$ is hydrogen.

The latter compound of formula Ib can be reduced with a complex metal hydride, preferably with about five to ten molar equivalents of borane in an inert organic solvent, preferably tetrahydrofuran or dioxane, at 60° to 70° C. for 15 to 30 hours to obtain the corresponding compound of formula Ib in which $R^3$, $R^4$, $R^{14}$ and $R^{15}$ are as defined herein, $R^{16}$ is a radical of formula $(CH_2)_nNR^{12}R^{13}$ wherein n, $R^{12}$ and $R^{13}$ are as defined herein, and $R^{17}$ is hydrogen.

The following examples illustrate further this invention.

EXAMPLE 1

1,3,4,10b-Tetrahydro-2-methylpyrimido[6,1-a]isoindol-6(2H)-one (Ib: $R^3$, $R^4$, $R^{14}$, $R^{16}$ and $R^{17}$=H, and $R^{15}$=Me)

Methyl lithium (104 ml of 2.2 M in diethyl ether) is added dropwise to a solution of 2,3-dihydro-3-oxo-1H-isoindole-1-acetic acid (described by F. M. Rowe et al., J. Chem. Soc., 1098 (1936), 10 g, 0.0524 mol) dissolved in 600 ml of dry tetrahydrofuran with stirring at room temperature. The reaction is stirred for 3 hr and poured into 200 ml of cold 10% hydrochloric acid. Most of the tetrahydrofuran is removed by evaporation and the residue is extracted with chloroform. The chloroform extract is washed with 5% sodium bicarbonate and water, dried and evaporated. The residue is chromatographed on silica gel using 30% acetone in benzene and the eluates are evaporated. The residue (5 g) is crystallized from benzene-petroleum ether to obtain 2,3-dihydro-3-oxo-1H-isoindole-1-propane-2'-one, mp 140°-142° C., Anal. Calc'd. for $C_{11}H_{11}NO_2$: C, 69.82% H, 5.86% N, 7.4% and Found: C, 69.97% H, 5.95% N, 7.13%.

A mixture of the latter compound (10 g, 0.053 mol), 7.5 g of hydroxylamine hydrochloride and 9.16 of potassium hydroxide in 610 ml of ethanol and 110 ml of water is refluxed for 10 min. The reaction is cooled with ice and most of the ethanol is removed by evaporation. The aqueous solution is extracted with chloroform. The chloroform extract is washed with water, dried and evaporated to afford 2,3-dihydro-3-oxo-1H-isoindole-1-propane-2-one 2-oxime (8.4 g).

To the latter compound (8.46 g, 0.0415 mol) in 200 ml of ethanol is added 12.7 g of Nickel-Aluminium alloy and 212 ml of 2 N sodium hydroxide while cooling, keeping the temperature during the addition of the sodium hydroxide at 20°-30° C. The reaction is stirred vigorously at room temperature for 1.5 hr, filtered through diatomaceous earth. Most of the ethanol is removed by evaporation and the residue is extracted with chloroform. The chloroform extract is washed with water, dried and evaporated to afford a yellow solid of 2,3-dihydro-3-oxo-1H-isoindole-1-(α-methyl)ethylamine (5 g), mp 118°-120° C.

A solution of the latter compound (5.0 g, 0.0263 mol) and 2.5 ml of 37% aqueous formaldehyde in 62 ml of ethanol is refluxed for 2.5 hr. The reaction is evaporated to dryness and the residue is chromatographed on silica gel using 2% methanol in chloroform. The eluates are evaporated and the residue (5.3 g) is crystallized from benzenepetroleum ether to give the title compound, mp 120°-121° C., Anal. Calc'd. for $C_{12}H_{14}N_2O$: C, 71.26% H, 6.98% N, 13.85% and Found: C, 71.17% H, 6.98% N, 13.55%. The title compound is treated with a solution of hydrogen chloride in diethyl ether. The precipitate is collected and crystallized from ethanol-diethyl ether to obtain the hydrochloride salt (3.3 g) of the title compound, mp 275°-280° C., Anal. Calc'd. for $C_{12}H_{14}N_2O \cdot HCl$: C, 60.37% H, 6.33% N, 11.74% and Found: C, 60.24% H, 6.33% N, 11.60%.

EXAMPLE 2

1,10b-Dihydro-2,2-dimethylpyrimido[6,1a]isoindol-6(2H)-one (Ib: $R^3$ and $R^4$=H, $R^{14}$ and $R^{15}$=Me, and $R^{16}$ and $R^{17}$ together form an imine)

A solution of 2,3-dihydro-3-oxo-1H-isoindole-1-acetic acid (described by F. M. Rowe et al., supra, 130 g, 0.682 mol) in methanol (1300 ml) containing 6.5 g of p-toluenesulfonic acid is refluxed with stirring for 3.5 hr. Most of the methanol is evaporated and the residue is dissolved in chloroform. The solution is washed with 5% aqueous sodium bicarbonate and water, dried and evaporated. The residue (125 g) is crystallized from isopropanol to give methyl 2,3-dihydro-3-oxo-1H-isoindole-1-acetate, mp 136°-138° C.

A solution of the latter compound (7.2 g, 0.035 mol) in 250 ml of tetrahydrofuran is added dropwise to a solution of methyl magnesium iodide (prepared from magnesium, 4.11 g, 0.075 gram-atoms and methyl iodide, 23.8 g, 0.168 mole, in 200 ml of diethyl ether). The reaction is refluxed for 18 hr with stirring, cooled and poured into 350 ml of ice-cold 10% sulfuric acid. The solution is extracted with chloroform and the chloroform extract is washed with 5% aqueous sodium bicarbonate and water, dried and evaporated. The residue is crystallized from benzene to give 2,3-dihydro-3-(2-hydroxy-2-methylpropyl)-1H-isoindol-1-one, which also is known as 1,3-dihydro-3-(2-hydroxy-2-methylpropyl)-2H-isoindole-1-one, (4.8 g), mp 122°-123° C., Anal. Calc'd. for $C_{12}H_{15}NO_2$: C, 70.22% H, 7.37% N, 6.82% and Found: C, 70.11% H, 7.37% N, 6.96%.

A solution of the latter compound (11.0 g, 0.0586 mol) and sodium cyanide (5.4 g, 0.11 mol) in 75 ml of acetic acid is stirred at 60° C. while a solution of 121 g of sulfuric acid and 66 ml of acetic acid is added dropwise. When the addition is complete, the reaction is stirred at room temperature for 4 hr. The reaction is poured into icewater (1000 ml) and the solution is extracted with chloroform. The chloroform extract is washed with 5% aqueous sodium bicarbonate and water, dried and evaporated. The residue is chromatographed on silica gel using 50% acetone in benzene and the eluates are evaporated to give 1,3,4,10b-tetrahydro-4-hydroxy-2,2-dimethylpyrimido[6,1-a]isoindol-6(2H)-one (5.5 g), nmr (CDCl$_3$) δ1.55(d), 1.7-2.8(m), 4.6-4.9(m), 6.5-6.7(m) and 7.3-8.3(m).

A mixture of the latter compound (3.0 g, 0.0129 mol) and 10 ml of thionyl chloride is refluxed with stirring for 2 hr and evaporated. The residue (2.5 g) is crystallized from isopropanol to give the hydrochloride salt (1.85 g) of the title compound, mp 285°–295° C. (dec), Anal. Calc'd. for $C_{13}H_{14}N_2O\cdot HCl$: C, 62.29% H, 5.63% N, 11.18% Cl, 14.15% and Found: C, 61.92% H, 5.99% N, 11.13% Cl, 13.97%.

In the same manner but replacing 2,3-dihydro-3-oxo-1H-isoindole-1-acetic acid with an equivalent amount of 6-ethyl-2,3-dihydro-3-oxo-1H-isoindole-1-acetic acid, 6-propoxy-2,3-dihydro-3-oxo-1H-isoindole-1-acetic acid, 5-trifluoromethyl-2,3-dihydro-3-oxo-1H-isoindole-1-acetic acid, 5-pentyl-2,3-dihydro-3-oxo-1H-isoindole-1-acetic acid or 6-bromo-2,3-dihydro-3-oxo-1H-isoindole-1-acetic acid, the following compounds of formula Ib are obtained, respectively: 9-ethyl-1,10b-dihydro-2,2-dimethylpyrimido[6,1-a]isoindole-6(2H)-one, 9-propoxy-1,10b-dihydro-2,2-dimethylpyrimido[6,1-a]isoindole-6(2H)-one, 8-trifluoromethyl-1,10b-dihydro-2,2-dimethylpyrimido[6,1-a]isoindole-6(2H)-one, 8-pentyl-1,10b-dihydro-2,2-dimethylpyrimido[6,1-a]isoindole-6(2H)-one and 9-bromo-1,10b-dihydro-2,2-dimethylpyrimido[6,1-a]isoindol-6(2H)-one.

EXAMPLE 3

1,3,4,10b-Tetrahydro-2,2-Dimethylpyrimido[6,1-a]isoindol-6(2H)-one (Ib: $R^3$, $R^4$, $R^{16}$ and $R^{17}$=H, and $R^{14}$ and $R^{15}$=Me)

Sodium borohydride (4.4 g, 0.126 mol) is added portionwise to a stirring solution of 1,10b-dihydro-2,2-dimethylpyrimido[6,1a]isoindol-6(2H)-one (described in Example 2, 8.0 g, 0.032 mol) in 150 ml of methanol. The mixture is refluxed for 1.5 hr and evaporated. Water is added and the solution is extracted with chloroform. The chloroform extract is washed with water, dried and evaporated. The residue is crystallized from benzene to give the title compound (6.9 g), mp 155°–156° C.

The title compound is treated with a solution of hydrogen chloride in diethyl ether. The precipitate is collected and crystallized from isopropanol to obtain the hydrochloride salt of the title compound, mp 303°–306° C., Anal. Calc'd. for $C_{13}H_{16}\text{-}N_2O\cdot HCl$: C, 61.77% H, 6.78% N, 11.08% Cl, 14.03% and Found: C, 61.81% H, 6.81% N, 11.06% Cl, 13.85%.

In the same manner but replacing 1,10b-dihydro-2,2-dimethylpyrimido[6,1-a]isoindol-6(2H)-one with an equivalent amount of another compound of formula Ib, described in Example 2, the following compounds of formula Ib are obtained, respectively: 9-ethyl-1,3,4,10b-tetrahydro-2,2-dimethylpyrimido[6,1-a]isoindole-6(2H)-one, 9-propoxy-1,3,4,10b-dihydro-2,2-dimethylpyrimido[6,1-a]isoindole-6(2H)-one, 8-trifluoromethyl-1,3,4,10b-dihydro-2,2-dimethylpyrimido[6,1-a]isoindole-6(2H)-one, 8-pentyl-1,3,4,10b-dihydro-2,2-dimethylpyrimido[6,1-a]isoindole-6(2H)-one and 9-bromo-1,3,4,10b-dihydro-2,2-dimethylpyrimido[6,1-a]isoindole-6(2H)-one.

EXAMPLE 4

3-(N,N-Dimethylaminoacetyl)-1,3,4,10b-tetrahydro-2,2-dimethylpyrimido[6,1-a]isoindol-6(2H)-one (Ib: $R^3$, $R^4$ and $R^{17}$=H, $R^{14}$ and $R^{15}$=Me, and $R^6$=COCH$_2$NMe$_2$)

Bromoacetyl bromide (10.86 g, 0.0537 mol) in 100 ml of benzene is added dropwise to an ice-cold stirring mixture of 1,3,4,10b-tetrahydro-2,2-dimethylpyrimido[6,1-a]isoindol-6(2H)-one hydrochoride (described in Example 3, 9.2 g, 0.0426 mol) and triethylamine (7.0 g, 0.0693 mol) in 500 ml of benzene. The reaction is stirred at room temperature for 18 hr and water is added. The organic phase is collected, washed with 5% hydrochloric acid, 5% sodium bicarbonate and water, dried and evaporated. The residue is chromatographed on silica gel using 30% acetone in benzene and the eluates are evaporated to give 3-(2-bromo-1-oxoethyl)-1,3,4,10b-tetrahydro-2,2-dimethylpyrimido[6,1-a]isoindol-6(2H)-one (9.9 g), nmr (CDCl$_3$) $\delta$1.5(s), 1.6(s), 2.0(m), 4.1(d), 4.7(d), 4.65(d), 5.85(d) and 7.7(m).

A solution of the latter compound (9.9 g, 0.0294 mol) in 600 ml of tetrahydrofuran is added dropwise to 100 ml of a stirring solution of 40% aqueous dimethylamine. The solution is stirred at 60° C. for 2 hr. Most of the tetrahydrofuran is removed by evaporation and water is added. The solution is extracted with chloroform and the chloroform extract is washed with 5% sodium bicarbonate and water, dried and evaporated to afford the title compound (9.8 g).

The maleate salt of the tile compound melts at 156°–160° C., Anal. Calc'd. for $C_{17}H_{12}N_3O_2\cdot C_4H_4\text{-}O_4$: C, 60.42% H, 6.52% N, 10.07% and Found: C, 60.33% H, 6.49% N, 10.16%.

In the same manner but replacing dimethylamine with an equivalent amount of ethylamine, dibutylamine, N-ethyl-N-propylamine or pentylamine and replacing bromoacetyl bromide with an equivalent amount of 4-chlorobutionyl chloride, the following compounds of formula Ib are obtained, respectively: 3-[4-(ethylamino)-butionyl]-1,3,4,10b-tetrahydro-2,2-dimethylpyrimido[6,1-a]isoindol-6(2H)-one, 3-[4-(N,N-dibutylamino)butionyl]-1,3,4,10b-tetrahydro-2,2-dimethylpyrimido[6,1-a]isoindol6(2H)-one, 3-[4-(N-ethyl-N-propylamino)-butionyl]-1,3,4,10b-tetrahydro-2,2-dimethylpyrimido[6,1-a]isoindol-6(2H)-one and 3-[4-(pentylamino)-butionyl]-1,3,4,10b-tetrahydro-2,2-dimethylpyrimido[6,1-a]isoindol-6(2H)-one.

Similarly, by replacing 1,3,4,10b-tetrahydro-2,2-dimethylpyrimido[6,1-a]isoindol-6(2H)-one with an equivalent amount of another compound of formula Ib, described in Example 3, the following compounds of formula Ib are obtained, respectively: 9-ethyl-3-(N,N-dimethylaminoacetyl)-1,3,4,10b-tetrahydro-2,2-dimethylpyrimido[6,1-a]isoindol-6(2H)-one, 9-propoxy-3-(N,N-dimethylaminoacetyl)-1,3,4,10b-tetrahydro-2,2-dimethylpyrimido[6,1-a]isoindol-6(2H)-one, 8-trifluoromethyl-3-(N,N-dimethylaminoacetyl)-1,3,4,10b-tetrahydro-2,2-dimethylpyrimido[6,1-a]isoindol-6(2H)-one, 8-pentyl-3-(N,N-dimethylaminoacetyl)-1,3,4,10b-tetrahydro-2,2-dimethylpyrimido[6,1-a]isoindol-6(2H)-one and 9-bromo-3-(N,N-dimethylaminoacetyl)-1,3,4,10b-tetrahydro-2,2-dimethylpyrimido[6,1-a]isoindol-6(2H)-one.

EXAMPLE 5

1,3,4,10b-Tetrahydropyrimido[6,1-a]isoindol-6(2H)-one (Ib: $R^3$, $R^4$, $R^{14}$, $R^{15}$, $R^{16}$ and $R^{17}$=H)

A mixture of 3-cyanomethylenephthalimidine (described by J. Kranz, Chem. Ber., 100, 2261 (1967), 19.2 g, 0.113 mol) and Raney nickel catalyst in ethanol saturated with ammonia is hydrogenated at 70° C. and 700 psi for 24 hr. The mixture is filtered and the filtrate is evaporated to give 3-aminoethyl-1-oxoisoindole, nmr (CDCl$_3$) $\delta$2.4(m), 3.0(m), 4.9(t) and 7.7(m). The hydrochloride salt (1.94 g) of the latter compound melts at 243°–248° C.

A solution of the latter salt (19.4 g, 0.0915 mol) and 37% aqueous formaldehyde (9 ml) in ethanol (320 ml) is refluxed for 2.5 hr and the ethanol is removed by evaporation. Aqueous sodium bicarbonate (5%) is added and the solution is extracted with chloroform. The chloroform extract is washed with water, dried and evaporated. The residue is chromatographed on silica gel using 10% methanol in chloroform and the eluates were evaporated to give the title compound (8.7 g).

The title compound is treated with a solution of hydrogen chloride in diethyl ether. The precipitate is collected and crystallized from isopropanol to obtain the hydrochloride salt of the title compound, mp 228°–235° C., Anal. Calc'd. for $C_{11}H_{11}N_2O \cdot HCl$: C, 58.80% H, 5.83% N, 12.47% Cl, 15.78% and Found: C, 58.78% H, 6.15% N, 12.45% Cl, 15.89%.

We claim:

1. A compound of formula Ib

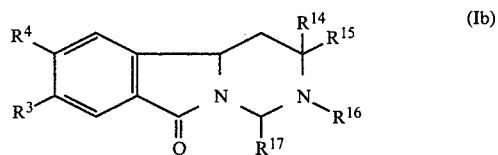

in which $R^3$ and $R^4$ each is hydrogen, lower alkoxy, lower alkyl, trifluoromethyl, halo, or hydroxy; or $R^3$ and $R^4$ together form a $OCH_2O$ chain; $R^{14}$ and $R^{15}$ each is hydrogen or lower alkyl; $R^{16}$ is hydrogen, a radical of formula $(CH_2)_nNR^{12}R^{13}$ wherein n is an integer from two to six, and $R^{12}$ and $R^{13}$ each is hydrogen or lower alkyl, or a radical of formula $CO(CH_2)_{n-1}NR^{12}R^{13}$ wherein n, $R^{12}$ and $R^{13}$ are as described herein, and $R^{17}$ is hydrogen, or $R^{16}$ and $R^{17}$ together form an imine; or a thereapeutically acceptable acid addition salt thereof.

2. A compound of formula Ib

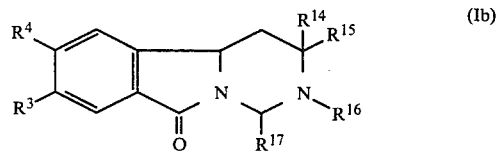

in which $R^3$ and $R^4$ are hydrogen; $R^{14}$ and $R^{15}$ each is hydrogen or lower alkyl; $R^{16}$ is hydrogen or a radical of formula $CO(CH_2)n-1NR^{12}R^{13}$ wherein n is an integer from two to six, and $R^{12}$ and $R^{13}$ each is lower alkyl; and $R^{17}$ is hydrogen, or $R^{16}$ and $R^{17}$ together form an imine; or a therapeutically acceptable acid addition salt thereof.

3. 1,3,4,10b-Tetrahydro-2-methylpyrimido[6,1-a]isoindol-6(2H)-one, as claimed in claim 1.

4. 1,10b-Dihydro-2,2-dimethylpyrimido[6,1-a]isoindol-6(2H)-one, as claimed in claim 1.

5. 1,3,4,10b-Tetrahydro-2,2-dimethylpyrimido[6,1-a]isoindol-6(2H)-one, as claimed in claim 1.

6. 3-(N,N-Dimethylaminoacetyl)-1,3,4,10b-tetrahydro-2,2-dimethylpyrimido[6,1-a]isoindol-6(2H)-one, as claimed in claim 1.

7. 1,3,4,10b-Tetrahydropyrimido[6,1-a]isoindol-6(2H)-one, as claimed in claim 1.

8. A method of treating hypertension in a mammal, which comprises administering to said mammal an effective antihypertensive amount of a compound of formula Ib or a therapeutically acceptable acid addition salt thereof, as claimed in claim 1.

9. An antihypertensive pharmaceutical composition, which comprises an effective amount of a compound of formula Ib or a therapeutically acceptable acid addition salt thereof, as claimed in claim 1, and a pharmaceutically acceptable carrier therefor.

10. A method of treating hypertension in an hypertensive mammal, which comprises administering to the mammal an antihypertensive effective amount of a compound of formula Ib of claim 1, or a therapeutically acceptable acid addition salt thereof, in combination with an effective amount of a diuretic and/or antihypertensive agent, in which the agent is chlorothiazide, hydrochlorothiazide or propranolol.

11. An antihypertensive pharmaceutical composition comprising an effective amount of a compound of formula Ib of claim 1, or a therapeutically acceptable acid addition salt thereof, and a diuretic and/or antihypertensive agent, in which the agent is chlorothiazide, hydrochlorothiazide or propranolol.

12. The method of claim 10 in which the compound of formula Ib or a therapeutically acceptable salt thereof, and the diuretic and/or antihypertensive agent is administered sequentially or simultaneously.

* * * * *